(12) United States Patent
Malik et al.

(10) Patent No.: US 7,449,210 B2
(45) Date of Patent: Nov. 11, 2008

(54) ELECTROSTATIC LOADING OF DRUGS ON IMPLANTABLE MEDICAL DEVICES

(75) Inventors: Shamim Malik, Temecula, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 453 days.

(21) Appl. No.: 11/204,549

(22) Filed: Aug. 15, 2005

(65) Prior Publication Data

US 2005/0273161 A1 Dec. 8, 2005

Related U.S. Application Data

(62) Division of application No. 10/306,648, filed on Nov. 26, 2002, now Pat. No. 6,982,004.

(51) Int. Cl.
*A61L 33/00* (2006.01)
*B05D 3/14* (2006.01)
*B05D 1/04* (2006.01)
*B05D 7/14* (2006.01)

(52) U.S. Cl. .............. 427/2.1; 427/2.24; 427/476; 427/457; 427/486; 427/533

(58) Field of Classification Search ......... 427/2.1–2.28, 427/476, 457, 486
See application file for complete search history.

(56) References Cited

U.S. PATENT DOCUMENTS

| | | | |
|---|---|---|---|
| 4,329,383 A | 5/1982 | Joh | |
| 4,361,418 A | 11/1982 | Tscheppe | |
| 4,628,859 A | 12/1986 | Hines | |
| 4,684,064 A | 8/1987 | Kwok | |
| 4,733,665 A * | 3/1988 | Palmaz | 606/108 |
| 4,800,882 A | 1/1989 | Gianturco | |
| 4,828,840 A | 5/1989 | Sakamoto et al. | |
| 4,882,168 A | 11/1989 | Casey et al. | |
| 4,886,062 A | 12/1989 | Wiktor | |
| 4,932,353 A | 6/1990 | Kawata et al. | |
| 4,941,870 A | 7/1990 | Okada et al. | |
| 4,977,901 A | 12/1990 | Ofstead | |
| 5,112,457 A | 5/1992 | Marchant | |
| 5,165,919 A | 11/1992 | Sasaki et al. | |
| 5,272,012 A | 12/1993 | Opolski | |

(Continued)

FOREIGN PATENT DOCUMENTS

EP 0 301 856 2/1989

(Continued)

OTHER PUBLICATIONS

Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).

(Continued)

*Primary Examiner*—William P. Fletcher, III
*Assistant Examiner*—Cachet I Sellman
(74) *Attorney, Agent, or Firm*—Squire, Sanders & Dempsey L.L.P.

(57) ABSTRACT

A method for electrostatic loading of drugs on an implantable medical device is disclosed.

12 Claims, 2 Drawing Sheets

U.S. PATENT DOCUMENTS

| | | |
|---|---|---|
| 5,279,863 A | 1/1994 | Escallon |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,328,471 A | 7/1994 | Slepian |
| 5,330,768 A | 7/1994 | Park et al. |
| 5,380,299 A | 1/1995 | Fearnot et al. |
| 5,399,198 A | 3/1995 | Ghaisas |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,569,463 A | 10/1996 | Helmus et al. |
| 5,578,073 A | 11/1996 | Haimovich et al. |
| 5,605,696 A | 2/1997 | Eury et al. |
| 5,609,629 A | 3/1997 | Fearnot et al. |
| 5,624,411 A | 4/1997 | Tuch |
| 5,628,730 A | 5/1997 | Shapland et al. |
| 5,641,358 A | 6/1997 | Stewart |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,679,400 A | 10/1997 | Tuch |
| 5,700,286 A | 12/1997 | Tartaglia et al. |
| 5,702,754 A | 12/1997 | Zhong |
| 5,716,981 A | 2/1998 | Hunter et al. |
| 5,735,897 A | 4/1998 | Buirge |
| 5,746,998 A | 5/1998 | Torchilin et al. |
| 5,776,184 A | 7/1998 | Tuch |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,919,126 A | 7/1999 | Armini |
| 5,925,720 A | 7/1999 | Kataoka et al. |
| 5,955,509 A | 9/1999 | Webber et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,010,573 A | 1/2000 | Bowlin |
| 6,015,541 A | 1/2000 | Greff et al. |
| 6,019,784 A | 2/2000 | Hines |
| 6,033,582 A | 3/2000 | Lee et al. |
| 6,042,875 A | 3/2000 | Ding et al. |
| 6,051,576 A | 4/2000 | Ashton et al. |
| 6,051,648 A | 4/2000 | Rhee et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,165,212 A | 12/2000 | Dereume et al. |
| 6,174,329 B1 | 1/2001 | Callol et al. |
| 6,203,551 B1 | 3/2001 | Wu |
| 6,231,600 B1 | 5/2001 | Zhong |
| 6,240,616 B1 | 6/2001 | Yan |
| 6,245,753 B1 | 6/2001 | Byun et al. |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,346,110 B2 | 2/2002 | Wu |
| 6,358,556 B1 | 3/2002 | Ding et al. |
| 6,379,381 B1 | 4/2002 | Hossainy et al. |
| 6,391,052 B2 | 5/2002 | Buirge et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,454,193 B1 | 9/2002 | Busick et al. |
| 6,457,470 B1 | 10/2002 | Coffee |
| 6,494,862 B1 | 12/2002 | Ray et al. |
| 6,503,481 B1 | 1/2003 | Thurston et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,527,801 B1 | 3/2003 | Dutta |
| 6,527,863 B1 | 3/2003 | Pacetti et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,765 B1 | 7/2003 | Hossainy et al. |
| 6,585,926 B1 | 7/2003 | Mirzaee |
| 6,605,154 B1 | 8/2003 | Villareal |
| 6,669,980 B2 | 12/2003 | Hansen |
| 6,743,462 B1 | 6/2004 | Pacetti |
| 6,743,463 B2 * | 6/2004 | Weber et al. ............... 427/2.24 |
| 2001/0018469 A1 | 8/2001 | Chen et al. |
| 2001/0037145 A1 | 11/2001 | Guruwaiya et al. |
| 2002/0077693 A1 | 6/2002 | Barclay et al. |
| 2002/0091433 A1 | 7/2002 | Ding et al. |
| 2002/0133224 A1 | 9/2002 | Bajgar et al. |
| 2002/0155212 A1 | 10/2002 | Hossainy |
| 2003/0054090 A1 | 3/2003 | Hansen |
| 2003/0065355 A1 | 4/2003 | Weber |
| 2003/0065377 A1 | 4/2003 | Davila et al. |
| 2003/0069634 A1 | 4/2003 | Bialecke et al. |
| 2003/0099712 A1 | 5/2003 | Jayaraman |
| 2003/0185964 A1 | 10/2003 | Weber et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |

| | | |
|---|---|---|
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

ELECTROSTATIC LOADING OF DRUGS ON IMPLANTABLE MEDICAL DEVICES

CROSS REFERENCE

This is a divisional of U.S. application Ser. No. 10/306,648 filed on Nov. 26, 2002 now U.S. Pat. No. 6,982,004.

BACKGROUND

This invention relates to an apparatus and method for electrostatic loading of a drug onto an implantable medical device such as a stent.

FIG. 1 illustrates a stent 10 having a conventional design of struts 12 interconnected by connecting elements 14. Struts 12 and connecting elements 14 are separated by gaps 16. Stent 10 is generally cylindrical and radially compressible. Compressible embodiments of stent 10 can be balloon expandable or self-expandable. Although stents work well mechanically, the chronic issues of restenosis and, to a lesser extent, thrombosis remain a significant clinical problem. These events are affected and made worse by the degree of injury and the hemodynamic disturbance caused by the stent. In order to more effectively treat these conditions, pharmacological therapy can be used in conjunction with stent therapy. Maintaining the necessary drug concentration at the lesion site for the necessary period of time remains a challenge, however. This can be done with brute force methods using oral or intravenous administration but the issues of systemic toxicity and side effects arise. Therefore, a preferred route can be achieved by local delivery of drug from the stent itself.

Being made of metal, plain stents are not useful for drug delivery. To serve as a drug reservoir, a coating, usually of a polymer, is applied by dipping or spraying the stent. A solution of a polymer dissolved in a solvent and a therapeutic substance added thereto is applied to the stent and the solvent is allowed to evaporate. A polymeric coating impregnated with a therapeutic substance then remains on the surface of the stent.

This manufacturing process can consume large quantities of solvent and process time. This process can also reduce the capability of batch processing (e.g., processing large stent quantities in single production runs) since each stent is individually sprayed with or dipped into the coating solution. Accordingly, a stent coating process is desired that reduces waste solvent and process time and can facilitate batch processing.

SUMMARY

A method of depositing a therapeutic substance on a stent is disclosed comprising ionizing a therapeutic substance; applying an electrical charge to a stent; and exposing the electrically charged stent to the ionized therapeutic substance. The therapeutic substance can be ionized by introducing a gas in a pressure chamber; applying pulsed bias voltage to a mesh tube surrounding the stent; applying RF power to a coil surrounding the mesh tube to produce electrons; and introducing the therapeutic substance into the chamber. The therapeutic substance can be introduced in bursts. The bias voltage applied to the mesh tube and the RF power can be turned off during the application of the electrical charge to the stent. The stent can be pre-coated with a primer layer.

A method for depositing a drug on a stent is disclosed comprising positioning a stent on a mandrel within a chamber, the mandrel being surrounded by a mesh tube and a coil; introducing a gas into the chamber; applying an RF power to the coil to produce electrons; applying an electrical charge to the mesh tube to collect the electrons around the stent; applying an electrical charge to the stent while terminating the application of the RF power to the coil and the electrical charge to the mesh tube; and supplying a drug into the chamber for ionizing the drug so that the drug is attracted to the stent. The drug can be supplied into the chamber by an inert carrier gas.

A method for depositing a drug onto a stent is disclosed comprising directing a drug towards a stent and operating a system including a coil surrounding the stent for charging the drug so that the drug is attracted to and deposited onto the stent. An electrical charge can be applied to the stent. In some embodiments, the system additionally includes a collecting member next to the stent, the collecting member capable of receiving a charge for collecting charged particles around the stent.

A method for depositing a drug onto a stent is disclosed comprising directing a charged drug towards a stent and operating a system including a collecting member positioned adjacent to the stent for collecting the charged drug around the stent. In some embodiments, the collecting member can be a mesh tube surrounding the stent. The method can include applying a charge to the stent and/or the collecting member.

DETAILED DESCRIPTION

Figure 1:
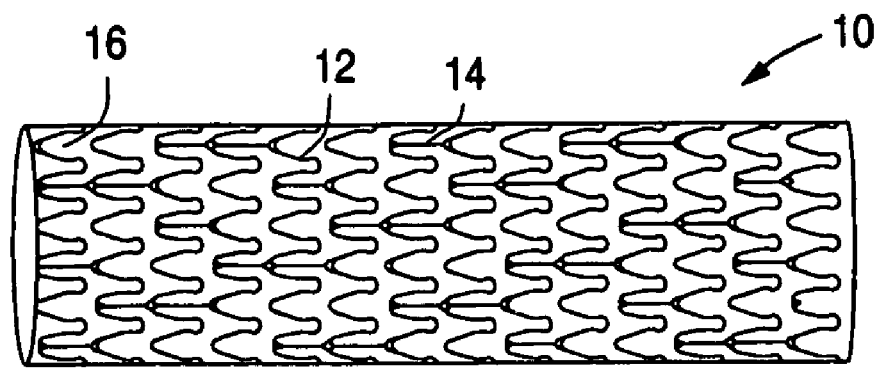
FIG. 1 illustrates a conventional stent.
Figure 2:
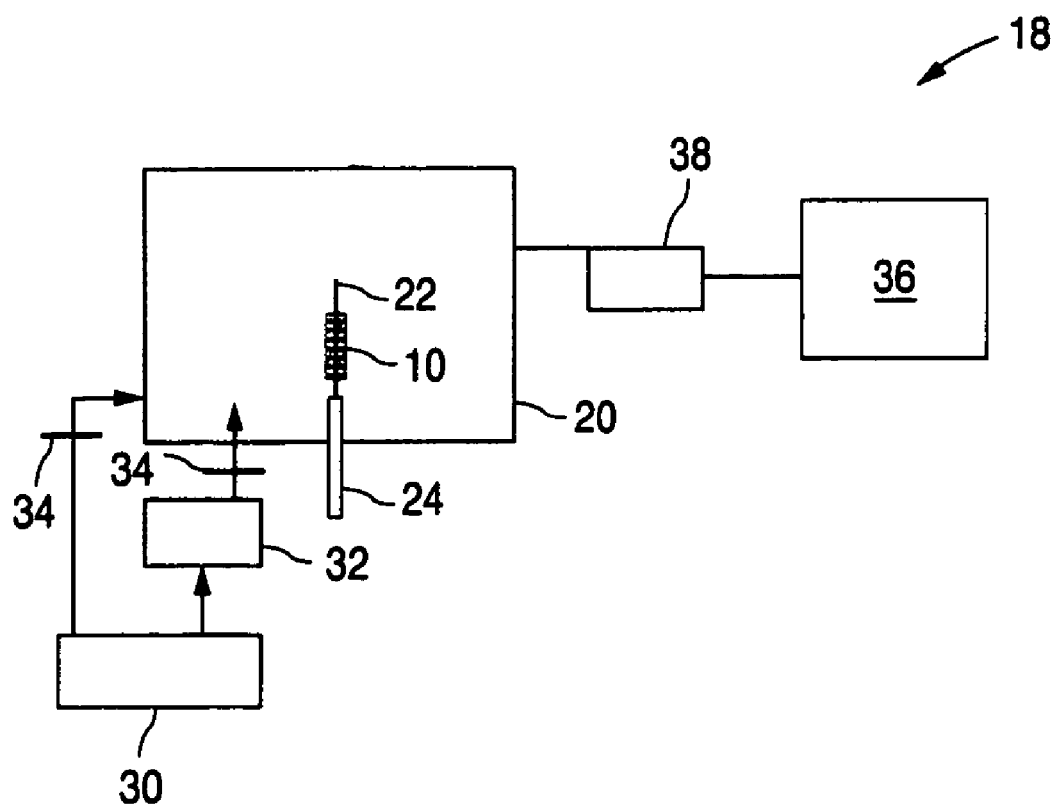
FIG. 2 is a schematic illustration of an embodiment of the coating system.
Figure 3:
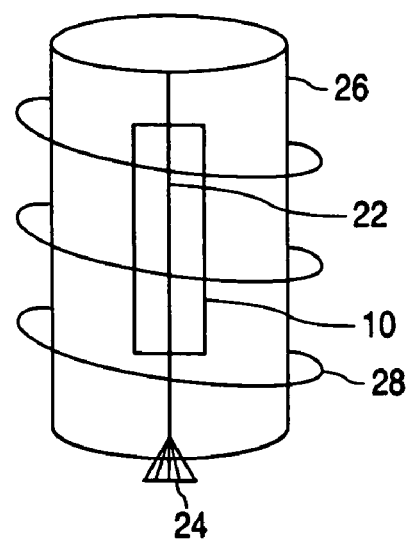
FIG. 3 is one embodiment of the mesh tube in which a stent can be placed surrounded by an RF coil.
Figure 4:
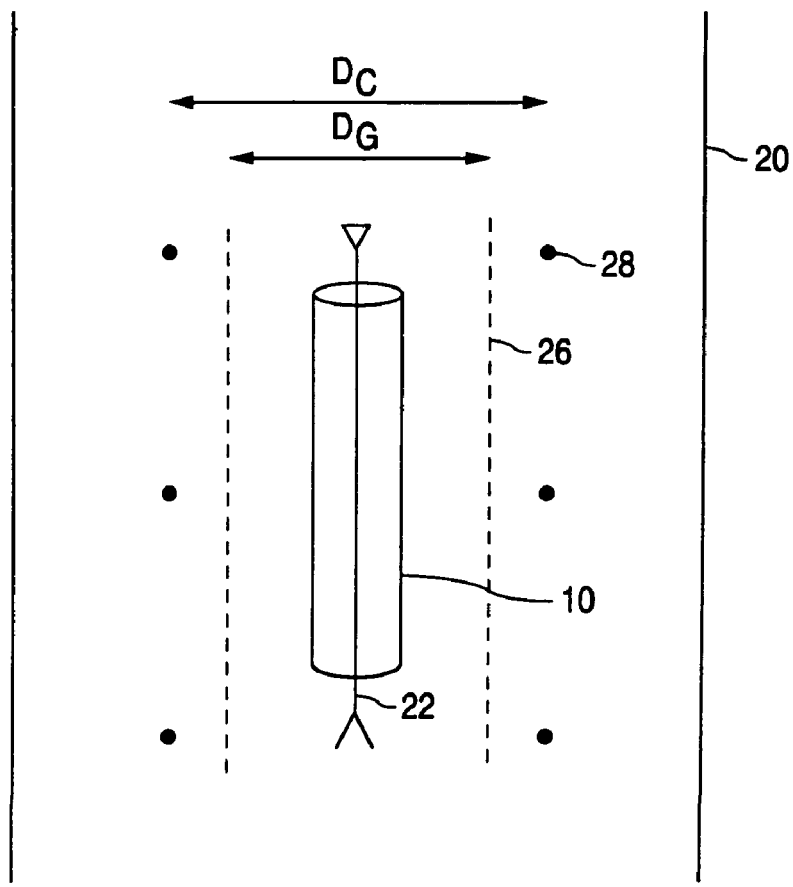
FIG. 4 is one embodiment of the stent, mesh tube, and RF coil inside of a pressure chamber.

FIG. 2 illustrates an embodiment of an agent loading apparatus 18, which includes a chamber 20 housing a stent support apparatus or mandrel 22 for supporting stent 10. Mandrel 22 is placed in electrical contact with an electrical feed 24 within chamber 20. Any suitable chamber 20 can be used, for example chambers that have electrical feed 24 mounted on a KF-40 flange (MDC, Hayward, Calif.). In one embodiment, as illustrated in FIG. 3, a grid or mesh tube 26 can circumscribe mandrel 22 and stent 10. Grid 26 can extract the electrons within the mesh tube and increase the uniformity of the coating surface. Grid 26 can have a tube diameter $D_G$ of about 2.5 cm and a thickness of about 0.1 mm. The surface area of the cylinder formed by grid or mesh tube 26 can be about 90% open voids and about 10% mesh. Mesh tube 26 can be connected to a second electrical feed, or can share electrical feed 24 with mandrel 22. An RF coil 28 circumscribes grid 26. The diameter $D_c$ of the coil can be about 5.1 cm.

Referring again to FIG. 2, a gas feed line 30 is in fluid communication with chamber 20 and a loading cavity 32, which in turn is in fluid communication with chamber 20. Loading cavity 32 holds the drugs in powder form. Closeable gates or valves 34 can be used to control the flow of the gas. A pump 36 can also be in fluid communication with chamber 20. Pump 36 can be a turbo pump, a mechanical rough pump, or a cryo pump. A particulate trap 38 can be disposed between pump 36 and chamber 20. One example of trap 38 is a Coaxial 4-line/Roughing Trap (from Varian Inc., Tempe, Ariz.) that attaches to a KF-40 flange. Trap 38 can minimize contamination in the exhaust from reaching pump 36. Trap 38 can filter particles from of up to, for example 10 microns (0.4 mils) in diameter.

One of ordinary skill in the art can understand that a plurality of stents 10 can be loaded onto mandrels 22 placed within chamber 20 in a grid-like or similar configuration to enable batch processing of stents 10. Additionally the medical device need not be limited to stents and a variety of other medical devices which need to be modified to delivery a drug can also be used.

A gas such as argon is introduced into chamber 20 and the pressure is maintained at about 50 to 100 mTorr. A pulsed bias of up to, for example, 50 V is applied to grid 26 while an RF power of, for example, 100 W at a frequency of 13.56 MHz is applied to initiate formation of electrons. Electrons are produced in chamber 20 while grid 26 collects the electrons around stent 10. Loading cavity 32 holds the drug in powder form having particles from about 1 micron (0.04 mils) to about 5 microns (0.2 mils) in diameter. The drug should be electrophilic to facilitate charging of the particles.

A carrier gas can then flow from gas feed line 30 through loading cavity 32, carrying the drug through gate 34 and into chamber 20. The gas should be inert to the biological properties of the drug. For example, gasses of helium, nitrogen, argon, neon, xenon, krypton, or combinations thereof can be used as the carrier. The drug is supplied in bursts, such as in 500 millisecond bursts into chamber 20 which, in effect, can raise the pressure in the chamber up to for example, 500 mTorr. The gas can be introduced at any temperature from about absolute zero to an upper limit temperature of the drug. The upper limit temperature of the drug is defined as the temperature above which the active agent begins to undergo substantial changes that permanently alter its biological efficacy. The upper limit temperature can be determined by one having ordinary skill in the art for each respective drug. Gate 34 can be opened and closed manually, or gate 34 can be closed automatically, for example when the pressure across gate 34 drops below a pre-determined level entered into a gate controller. The pulsed bias applied to grid 26 and RF power are tuned off and a pulsed bias is applied to stent 10 via mandrel 22, for example up to about 50 KV. As a result, the ionized drug is deposited on stent 10.

Stent 10 can be pre-coated with an appropriate coating, for example a carbon pre-coating or deposits or a primer polymer layer, to help adhere the substance to stent 10. The particles can then be compacted onto the surface of stent 10 or on the primer layer. It is believed that this coating method may produce a coating with a thickness from about 0.25 microns (0.0098 mils) to about 3 microns (0.1 mils) with a uniformity with less than about 5% variation in thickness.

Agent loading apparatus 18 and the coating method described herein can be used in conjunction with rotary atomizer or spray chilling apparatuses that coat stent 10 with polymers or polymer and agent combinations. Agent loading apparatus 18 can load an agent onto stent 10 before stent 10 is coated with a polymer or polymer and agent topcoating by a different process. The use of the inventive process and a complementary process can minimize the use of solvents for the agent application processes and enable the coating of large quantities of stents 10 in single batches.

The substance loaded onto the stent can be, for example, any drug capable of inhibiting abnormal or inappropriate migration and/or proliferation of smooth muscle cells for the prevention or inhibition of restenosis. The drug can also be capable of exerting a therapeutic or prophylactic effect such as for example enhancing wound healing in a vascular site or improving the structural and elastic properties of the vascular site.

While particular embodiments of the present invention have been shown and described, it will be obvious to those skilled in the art that changes and modifications can be made without departing from this invention in its broader aspects. Therefore, the appended claims are to encompass within their scope all such changes, modifications, and combinations as fall within the true spirit and scope of the invention.

What is claimed is:

1. A method of depositing a therapeutic substance on a stent, comprising:
   ionizing a therapeutic substance;
   applying an electrical charge to a stent; and
   exposing the electrically charged stent to the ionized therapeutic substance;
   wherein
   the therapeutic substance is ionized by introducing a gas in a pressure chamber;
   applying pulsed bias voltage to a mesh tube surrounding the stent;
   applying RF power to a coil surrounding the mesh tube to produce electrons; and
   introducing the therapeutic substance into the chamber.

2. The method of claim 1, wherein the therapeutic substance is introduced in bursts.

3. The method of claim 1, wherein the bias voltage applied to the mesh tube and the RF power are turned off during the application of the electrical charge to the stent.

4. A method of depositing a therapeutic substance on a stent, comprising:
   ionizing a therapeutic substance;
   applying an electrical charge to a stent; and
   exposing the electrically charged stent to the ionized therapeutic substance;
   wherein the stent is pre-coated with a primer layer.

5. A method for depositing a drug on a stent, comprising: positioning a stent on a mandrel within a chamber, the mandrel being surrounded by a mesh tube and a coil; introducing a gas into the chamber; applying a RF power to the coil to produce electrons; applying an electrical charge to the mesh tube to collect the electrons around the stent; applying an electrical charge to the stent while terminating the application of the RF power to the coil and the electrical charge to the mesh tube; and supplying a drug into the chamber for ionizing the drug so that the drug is attracted to the stent.

6. The method of claim 5, wherein the drug is supplied into the chamber by an inert carrier gas.

7. A method for depositing a drug onto a stent, comprising:
   directing a drug towards a stent; and
   operating a system including a coil surrounding the stent for charging the drug so that the drug is attracted to and deposited onto the stent.

8. The method of claim 7, additionally comprising applying an electrical charge to the stent.

9. The method of claim 7, wherein the system additionally includes a collecting member next to the stent for collecting charged particles around the stent.

10. The method of claim 9, wherein the collecting member is located between the stent and the coil.

11. A method for depositing a drug onto a stent, comprising:
   directing a charade drug towards a stent; and
   operating a system including a collecting member positioned adjacent to the stent for collecting the charged drug around the stent;
   wherein the collecting member is a mesh tube surrounding the stent.

12. The method of claim 11, additionally comprising applying a charge to the stent and/or the collecting member.

* * * * *